(12) United States Patent
Goshen

(10) Patent No.: US 11,205,509 B2
(45) Date of Patent: Dec. 21, 2021

(54) IMAGE FEATURE ANNOTATION IN DIAGNOSTIC IMAGING

(71) Applicant: KONINKLIJKE PHILIPS N.V., Eindhoven (NL)

(72) Inventor: Liran Goshen, Pardes-Hanna (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 59 days.

(21) Appl. No.: 16/753,792

(22) PCT Filed: Oct. 2, 2018

(86) PCT No.: PCT/EP2018/076748
§ 371 (c)(1),
(2) Date: Apr. 5, 2020

(87) PCT Pub. No.: WO2019/068689
PCT Pub. Date: Apr. 11, 2019

(65) Prior Publication Data
US 2020/0258615 A1    Aug. 13, 2020

(30) Foreign Application Priority Data
Oct. 5, 2017   (EP) ...................................... 17194999

(51) Int. Cl.
*G06K 9/00*    (2006.01)
*G16H 30/40*   (2018.01)
(Continued)

(52) U.S. Cl.
CPC ........... *G16H 30/40* (2018.01); *G06T 7/0014* (2013.01); *G06T 7/11* (2017.01); *G06T 11/008* (2013.01);
(Continued)

(58) Field of Classification Search
CPC .................... G06N 3/0454; G06N 3/08; G06T 2207/10081; G06T 2207/20081;
(Continued)

(56) References Cited

U.S. PATENT DOCUMENTS 8,938,110 B2   1/2015 Goshen
2005/0010106 A1*  1/2005 Lang ...................... A61B 6/469
                                                       600/425
(Continued)

FOREIGN PATENT DOCUMENTS

CN        105640577 A    6/2016
WO    WO2015196300 A1   12/2015

OTHER PUBLICATIONS

PCT International Search Report, International application No. PCT/EP2018/076748, dated Nov. 23, 2018.
(Continued)

*Primary Examiner* — Xin Jia
(74) *Attorney, Agent, or Firm* — Larry Liberchuk

(57) ABSTRACT

The present invention relates to an image processing device (10) comprising a data input (11) for receiving volumetric image data comprising a plurality of registered volumetric images of an imaged object, a noise modeler (12) for generating a noise model indicative of a spatial distribution of noise in each of the plurality of registered volumetric images, a feature detector (13) for detecting a plurality of image features taking the volumetric image data into account, and a marker generator (14) for generating a plurality of references indicating feature positions of a subset of the plurality of detected image features, in which said subset corresponds to the detected image features that are classified as difficult to discern on a reference volumetric image in the plurality of registered volumetric images based on a classification and/or a visibility criterium, wherein the
(Continued)

classification and/or the visibility criterium takes the or each noise model into account.

13 Claims, 3 Drawing Sheets

(51) Int. Cl.
 G06T 7/11 (2017.01)
 G06T 7/00 (2017.01)
 G06T 11/00 (2006.01)
 G06T 15/08 (2011.01)
(52) U.S. Cl.
 CPC .... *G06T 15/08* (2013.01); *G06T 2207/10081* (2013.01); *G06T 2207/30168* (2013.01)
(58) Field of Classification Search
 CPC . G06T 2207/20084; G06T 2207/20152; G06T 2207/30061; G06T 5/008; G06T 5/20; G06T 7/0012; G06T 7/11; G06T 7/136; G06T 7/194; G16H 30/40; G16H 50/20
 See application file for complete search history.

(56) References Cited

U.S. PATENT DOCUMENTS

| | | | |
|---|---|---|---|
| 2010/0303358 A1 | 12/2010 | Acharyya | |
| 2015/0379694 A1* | 12/2015 | Goshen | A61B 6/482 382/195 |
| 2016/0328855 A1* | 11/2016 | Lay | G06K 9/4614 |
| 2017/0032522 A1* | 2/2017 | Quellec | G06T 7/0016 |
| 2017/0039685 A1 | 2/2017 | Goshen | |
| 2017/0281112 A1* | 10/2017 | Pack | G06T 11/005 |

OTHER PUBLICATIONS

Wunderlich A. et al., "Image Covariance and Lesion Detectability in Direct Fan-Beam X-Ray Computed Tomography," Physics in Medicine & Biology, 53(10), 2008, pp. 2472-2493.

Lindeberg T. et al., "Feature Detection with Automatic Scale Selection," International Journal of Computer Vision, 30.2 (1998): 79-116.

Lowe D. G. et al., "Distinctive Image Features From Scale-Invariant Keypoints," International Journal of Computer Vision, 60.2 (2004): 91-110.

Matas J. et al., "Robust Wide-Baseline Stereo from Maximally Stable Extremal Regions," Image and Vision Computing, 22.10 (2004): 761-767.

Potretke T. A. et al., "Early Small Bowel Ischemia: Dual-Energy CT Improves Conspicuity Compared with Conventional CT in a Swine Model", Radiology, vol. 275, No. 1, pp. 119-126, 2014.

Pinto A. et al., "Spectrum of Diagnostic Errors in Radiology." World Journal of Radiology, vol. 2, issue 10, Oct. 2010, pp. 377-383.

Lee, C. S. et al., "Cognitive and System Factors Contributing to Diagnostic Errors in Radiology." American Journal of Roentgenology, 201.3 (2013): 611-617.

Berlin L. et al., "Accuracy of Diagnostic Procedures: Has it Improved Over the Past Five Decades?" American Journal of Roentgenology, 188.5 (2007): 1173-1178.

Berlin L. et al., "Malpractice and Radiologists in Cook County, IL: Trends in 20 Years of Litigation", American Journal of Roentgenology, Oct. 1995; vol. 165, No. 4, pp. 781-788.

Johnson T. et al., "Dual Energy CT in Clinical Practice", Medical Radiology/Diagnostic Imaging, Springer, 2011, Part I—pp. 43-51, Part II—pp. 55-79.

\* cited by examiner

IMAGE FEATURE ANNOTATION IN DIAGNOSTIC IMAGING

FIELD OF THE INVENTION

The invention relates to the field of digital image processing of diagnostic images. More specifically it relates to image processing and image feature detection in a plurality of registered volumetric images, e.g. a plurality of corresponding volumetric images of an object obtained in a single imaging acquisition or a single imaging protocol, such as a plurality of spectral computed tomography images of the object, and to diagnostic image annotation.

BACKGROUND OF THE INVENTION

Diagnostic radiology aims at a complete detection of all abnormalities in an imaging examination and at an accurate diagnosis thereof. However, retrospective error rates in radiologic examinations can be quite high. Overall, approximately 30% of abnormal radiographic studies may remain undetected, where approximately 4% of radiologic interpretations rendered by radiologists in daily practice tend to contain errors. Therefore, a large portion of all medical malpractice claims against radiologists may be related to diagnostic errors. As medical reimbursements decrease, radiologists may attempt to compensate by undertaking additional responsibilities to increase productivity. The increased workload, rising quality expectations, cognitive biases, and poor system factors may all contribute to diagnostic errors in radiology and to an increased probability that a finding may be overlooked. As a result, there is an increased demand to improve the diagnostic reading environment and tools.

The range of available imaging modalities and the increasing sophistication of imaging technology and protocols, tends to provide the radiologist with a large amount of potentially useful images to be evaluated concurrently, typically in the form of multiple volumetric images that are registered, e.g. such that corresponding voxels of these images relate to a same location in the imaged object, yet can provide complementary information about the voxel location. Such images may be registered by applying a registration technique, as known in the art, or may be automatically registered by the very nature of the imaging technology and/or protocol involved. For example, the images may be acquired concurrently and/or simultaneously such that each voxel in the images relates to substantially a same position in the imaged object at substantially a same point of time. An example of such imaging modality that is capable of inherently providing registered images is spectral computed tomography (Spectral CT). Using a different point of view, such plurality of registered or concurrently acquired images may equivalently be considered as an image in which each voxel location has an associated vector-valued, i.e. non-scalar, voxel value. While a plurality of registered images and a voxel-valued image may or may not be stored differently in a digital storage memory in practice, a plurality of registered volumetric images and a volumetric voxel-valued image are considered equivalent in the context of the present description.

Spectral CT is an imaging modality that extends the capabilities of conventional CT. For example, in Dual-Energy (DE) CT, which is a specific configuration of spectral CT, for example image voxel, two attenuation values are acquired simultaneously at two photon energies, such that the photoelectric and Compton contributions to the mass attenuation properties of a material can be determined. This enables an identification of the material or materials present in each voxel by these photoelectric and Compton contributions. It is known in the art to perform dual-energy CT acquisitions by various means and methods, such as dual-source imaging, fast peak tube voltage (kVp) switching, and/or imaging using a dual-layer detector configuration.

It is also known in the art that spectral CT works particularly well in materials, such as iodine, that have a k-edge energy close to the mean value of a diagnostic imaging energy range. Because any two linearly independent sums of two basis functions span the entire attenuation coefficient space, any material can be represented by a linear combination of two other materials, so-called basis materials, for example water and iodine. The basis material images can be manipulated to provide new representations and/or visualizations, such as monochromatic images, material cancellation images, effective atomic number images and/or electron density images. Thus, the additional spectral information obtainable by spectral CT can augment the available quantitative information for analysis that can be measured about the scanned object and its material composition.

US 2010/303358 discloses a method for the automatic analysis of image data of a structure. An image in the form of a three-dimensional voxel array is segmented to determine a voxel subset, features are extracted for voxels from the voxel subset to generate a feature map and a scalar difference map is generated on the basis of the feature map. A classification is performed with the aid of the difference map and a structural anomaly in the image data is identified based on the classification.

SUMMARY OF THE INVENTION

It is an object of embodiments of the present invention to provide good and efficient means and methods for allowing a user, e.g. a radiologist, to evaluate a plurality of registered volumetric images, e.g. volumetric images that are co-registered by application of a registration algorithm and/or that are naturally registered by the nature of the imaging technology and/or protocol involved.

The above objective is accomplished by a method and device according to the present invention.

It is an advantage of embodiments of the present invention that a user is alerted in situations where a finding could not be seen or could barely be seen in a reference image, e.g. a conventional CT images, while it can be more easily seen in another image, e.g. in a corresponding spectral CT image.

It is an advantage of embodiments of the present invention that an effective and/or efficient reading tool is provided for use in medical diagnostics, e.g. in radiology and/or nuclear medicine.

It is an advantage of embodiments of the present invention that a chance that a finding is overlooked can be reduced, as compared to a conventional reading of a diagnostic image or image set.

It is an advantage of embodiments of the present invention that these can result in an advantageously low reading time and effort for the user, e.g. a radiologist. For example, the reading time and effort may be reduced compared to a conventional reading of a diagnostic image set.

It is an advantage of embodiments of the present invention that said advantages with respect to time, effort and/or probability in missing a finding can be particularly relevant for spectral CT, where quite a few spectral results may be made available to the user, e.g. a radiologist. For example, in a typical scenario, nine or more spectral results, e.g.

spectral image series, may be generally available. Reading these additional results can significantly increase the reading time and effort.

In a first aspect, the present invention relates to an image processing device comprising a data input for receiving volumetric image data organized in voxels. The volumetric image data comprises a plurality of registered volumetric images of an imaged object. The device comprises a noise modeler for generating at least one noise model indicative of a spatial distribution of noise in each of the plurality of registered volumetric images, e.g. generating a noise model for each of the plurality of registered volumetric images. The device comprises a feature detector for detecting a plurality of image features taking the volumetric image data into account. The device also comprises a marker generator for generating a plurality of references indicating feature positions, or positions and corresponding scales, of a subset of the plurality of detected image features. This subset corresponds to the detected image features that are classified as difficult to discern on a reference volumetric image in the plurality of registered volumetric images based on a classification and/or a numerical visibility criterium, e.g. a numerical classification and/or a numerical visibility criterium. The classification and/or the visibility criterium takes the or each noise model into account.

In a device in accordance with embodiments of the present invention, the data input may be adapted for receiving the volumetric image data in the form of the plurality of registered volumetric images obtained and/or derived from a single spectral computed tomography acquisition sequence.

In a device in accordance with embodiments of the present invention, the reference volumetric image may be representative of a conventional computed tomography image as obtained by or derived from the spectral computed tomography acquisition sequence.

In a device in accordance with embodiments of the present invention, the feature detector may be adapted for identifying a location and a scale of each detected image feature, and in the marker generator may be adapted for determining a plurality of visibility criteria for each detected feature taking the identified location and the identified scale of each detected image feature into account.

In a device in accordance with embodiments of the present invention, the marker generator may be adapted for classifying a detected feature as difficult to discern on the reference volumetric image if a predetermined number of said visibility criteria is met.

In a device in accordance with embodiments of the present invention, the marker generator may be adapted for estimating a contrast to noise ratio for each image feature in at least the image in which the image feature was detected and/or for estimating a contrast to noise ratio for each image feature in the reference image.

In a device in accordance with embodiments of the present invention, the marker generator may be adapted for, for each image feature, calculating a standard deviation of the voxel values in a region around the location of the image feature in the image in which the image feature was detected.

In a device in accordance with embodiments of the present invention, the marker generator may be adapted for, for each image feature, calculating a normalized cross-correlation and/or a mutual information between regions around the location of the image feature in respectively the reference image and at least the image in which the image feature was detected.

A device in accordance with embodiments of the present invention may comprise a segmentation unit for performing a segmentation of the structure corresponding to a detected feature in at least the image in which the feature was detected.

In a device in accordance with embodiments of the present invention, the feature detector may be adapted for calculating, for each of the plurality of volumetric images or each of a subset thereof, a scale-normalized Laplacian of Gaussian.

In a device in accordance with embodiments of the present invention, the noise modeler may be adapted for estimating the noise model using a Monte-Carlo estimation method, an analytical method and/or a direct extraction technique In a second aspect, the present invention also relates to a computed tomography workstation comprising an image processing device in accordance with embodiments of the first aspect of the present invention.

In a third aspect, the present invention also relates to a spectral computed tomography system comprising an image processing device in accordance with embodiments of the first aspect of the present invention.

In a fourth aspect, the present invention also relates to a method for generating a plurality of references indicating image features that are classified as difficult to discern on a reference volumetric image. The method comprises receiving volumetric image data organized in voxels, said volumetric image data comprising a plurality of registered volumetric images of an imaged object. The method comprises generating a noise model indicative of a spatial distribution of noise in each of the plurality of registered volumetric images. The method comprises detecting a plurality of image features taking the volumetric image data into account. The method comprises generating the plurality of references indicating feature positions of a subset of the plurality of detected image features, in which this subset corresponds to the detected image features that are classified as difficult to discern on a reference volumetric image in the plurality of registered volumetric images based on a (e.g. numerical) classification and/or a (e.g. numerical) visibility criterium. The classification and/or the visibility criterium takes the or each noise model into account.

In a fifth aspect, the present invention also relates to a computer readable storage medium encoded with one or more computer executable instructions, which, when executed by a processor of a computing system, causes the computing system to perform a method in accordance with embodiments of the fourth aspect of the present invention. Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
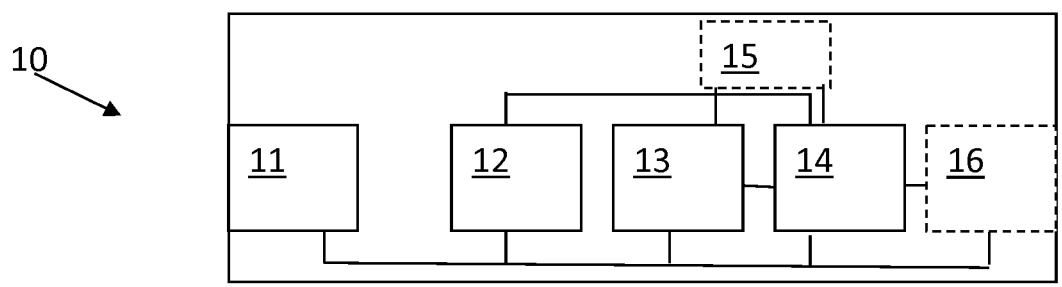
FIG. 1 schematically shows a device in accordance with embodiments of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In a first aspect, the present invention relates to an image processing device comprising a data input for receiving volumetric image data organized in voxels, in which the volumetric image data comprises a plurality of registered volumetric images of an imaged object. The device comprises a noise modeler for generating a noise model indicative of a spatial distribution of noise in the plurality of registered volumetric images, and a feature detector for detecting a plurality of image features taking the volumetric image data into account. The device also comprises a marker generator for generating a plurality of references indicating feature positions of a subset of the plurality of detected image features, in which the subset corresponds to the detected image features that are classified as difficult to discern on a reference volumetric image in the plurality of registered volumetric images based on a (e.g. numerical) classification or a (e.g. numerical) visibility criterion. The classification and/or the criterium takes the noise model into account.

Where in embodiments of the present invention reference is made to "registered volumetric images", reference is made to images in which corresponding voxel locations provide complementary information about a common position in an imaged object. The registered volumetric images may be obtained by the application of an image registration algorithm and/or may be obtained inherently by an imaging technique that simultaneously or concurrently obtains non-scalar data for each imaged voxel location.

Referring to FIG. 1, an image processing device 10 in accordance with embodiments of the present invention is schematically shown. The image processing device may comprise a computing device, such as a computer programmed for providing the functionality as described hereinbelow. The computing device may comprise a configurable hardware device, e.g. a field-programmable gate array, configured for providing the intended functionality or may comprise application specific circuitry specifically designed for providing the intended functionality. The computing device may comprise any combination of designed hardware, configured hardware and/or software for executing on general purpose hardware.

Thus, components of an image processing device 10 in accordance with embodiments of the present invention, as described hereinbelow, do not necessarily correspond to physically separate entities of such device, e.g. physically separable components, but may refer to a software construct that is implemented in a computer code for executing on a general purpose computer.

The device comprises a data input 11 for receiving the volumetric image data organized in voxels. Particularly, the data input may comprise a digital communication circuit, such as a computer network interface, a wireless transmission interface or a digital data bus interface, for receiving the data from an external source, such as a spectral CT scanner or a reconstructor for reconstructing CT images provided by a spectral CT scanner. The data input may comprise a virtual interface for receiving the data from another software component implemented on a shared hardware platform, e.g. from another software component executing on the same computer, such as a software component for reconstructing spectral CT image data. Such virtual interface may for example comprise an application programming interface, a shared memory resource or a file stored using a filesystem standard on a data carrier. The data input may comprise an interface for accessing a data carrier, such as an optical disk reader, a universal serial bus (USB) connection for accessing a USB data storage medium, a magnetic disk reader or a portable flash drive reader. The data input may comprise any combination of the means mentioned hereinabove, and/or other devices known in the art suitable for receiving digital volumetric image data.

The volumetric image data is organized in voxels, e.g. comprising a plurality of data values linked to corresponding voxel locations in a scanned object, e.g. a scanned subject. The volumetric image data may thus comprise reconstructed image data organized in voxels, e.g. representative of different positions in the scanned object with respect to a three-dimensional coordinate system. The volumetric image data may also comprise volumetric image data derived, e.g. calculated from, such reconstructed image data organized in voxels.

The volumetric image data comprises a plurality of registered volumetric images of an imaged object, e.g. a part of the body of a subject. Particularly, the volumetric image data may comprise diagnostic volumetric images, e.g. volumetric images obtained in a medical analysis in radiology and/or nuclear medicine.

The data input 11 may be adapted for receiving the volumetric image data in the form of the plurality of registered volumetric images obtained and/or derived from a single spectral computed tomography acquisition sequence. In other words, the plurality of registered volumetric images may be a plurality of 3D spectral CT images, e.g. reconstructed 3D spectral CT images obtained from a single spectral CT examination. The 3D spectral CT images may comprise a conventional CT image, e.g. an image obtained from the spectral data that is representative of a conventional non-spectral CT scan. The 3D spectral CT images may comprise a monochromatic image, a material image, such as an iodine map, a virtual non-contrast image, an effective atomic number image, a material cancellation image, an electron density image and/or other similar images derivable from a spectral CT scan. For example, the plurality of images may be obtained by or derived from a dual energy scanning approach known in the art, e.g., by a CT scanner having a dual-source configuration, adapted for performing a fast kVp switching scan and/or having a dual-layer detector configuration.

Each voxel may have a value associated therewith, e.g. a greyscale value such as a value expressed in Hounsfield units, that is indicative of attenuation characteristics of the scanned object at the position corresponding to the voxel, e.g. indicative of a radiodensity, e.g. of a relative radiodensity. The volumetric image data may comprise at least two different greyscale values associated with the same voxel location, e.g. for each voxel location. Each of the at least two different greyscale values may thus be indicative of different attenuation characteristics at the corresponding voxel location, e.g. for different qualities of penetrating ionizing radiation. The different qualities of penetrating ionizing radiation may differ sufficiently in mean and/or peak photon energy such that the different attenuation characteristics may be subject to discernibly different photoelectric effect and Compton effect contributions, e.g. indicative of different tissues and/or tissue properties in the subject. However, the different greyscale values need not correspond to, or be limited to, attenuation characteristics directly related to qualities of penetrating ionizing radiation the subject was exposed to in order to acquire the image data. For example, at least one of the different greyscale values (e.g. for each voxel) may be representative for an abstracted material property that was not directly observed, but inferred by combining and/or manipulating the directly acquired or reconstructed images. For example different scalar values per voxel may, in some embodiments, correspond to an arbitrary basis decomposition, as opposed to corresponding to physical energy spectra of ionizing radiation and/or detector characteristics used in scanning the object. For example, such scalar values may form a 80 kVp and/or a 120 kVp component image, a water-material, a bone-material and/or an iodine image and/or a monochromatic virtual image.

In embodiments, the plurality of registered volumetric images may comprise volumetric magnetic resonance images, volumetric computed tomography images, volumetric nuclear medicine images, volumetric echography images and/or other volumetric diagnostic images, e.g. medical images. The plurality of registered volumetric images may comprise multi-modality images or different volumetric images obtained by a single imaging modality.

Figure 2:
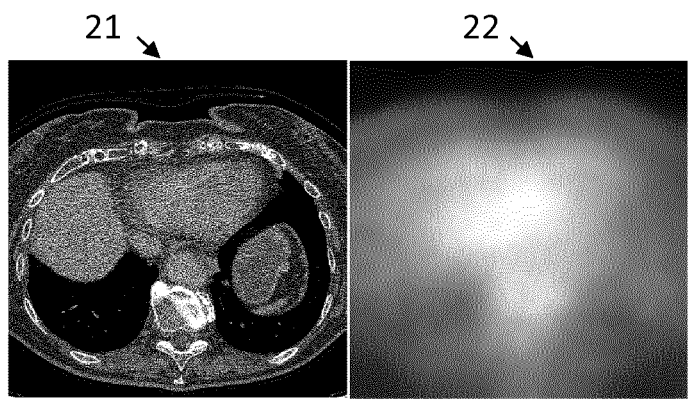
FIG. 2 shows a computed tomography (CT) image and a noise image generated from said computed tomography image, in accordance with embodiments of the present invention.

The device 10 comprises a noise modeler 12 for generating a noise model, e.g. a dataset noise pattern n, e.g. a noise estimation map or image, indicative of a spatial distribution of noise in each of the plurality of registered volumetric images. Referring to FIG. 2, an exemplary slice of a volumetric CT image 21 and a corresponding slice of a noise estimation map 22 are shown. The noise modeler 12 may be adapted for estimating the noise model using a Monte-Carlo estimation method, an analytical method and/or a direct extraction technique, as known in the art. For example, the noise modeler 12 may be adapted for implementing a noise estimation as disclosed in Wunderlich and Noo, "Image Covariance and Lesion Detectability in Direct Fan-Beam X-Ray Computed Tomography," Phys. Med. Biol. 53 (2008), 2472-2493, and/or as disclosed in the patent application US 2017/0039685, and/or as disclosed in the patent U.S. Pat. No. 8,938,110, which are incorporated herein by reference. However, other approaches are also contemplated herein.

The device 10 also comprises a feature detector 13 for detecting a plurality of image features taking the volumetric image data into account. The plurality of image features may for example, at least potentially, correspond to lesions, cysts, tumours, diseased tissue and/or local deviations in structure or texture. Thus, the features may identify, e.g. correspond to, key points in the images, which may be potential locations of structures of interest.

The features may be detected by a joint analysis of the plurality of volumetric images, or a subset of the plurality of volumetric images, or an analysis of each or some of the plurality of volumetric images separately.

Detecting the plurality of image features may comprise identifying a location, or a location and a scale, of each detected image feature.

For example, the feature detector 13 may be adapted for implementing a region or blob detection method, e.g. for each of the plurality of volumetric images, or each of a subset thereof, such as disclosed in Lindeberg, Tony, "Feature detection with automatic scale selection," International journal of computer vision 30.2 (1998): 79-116, in Lowe, David G., "Distinctive image features from scale-invariant keypoints," International journal of computer vision 60.2 (2004): 91-110 and/or in Matas, Jiri et al, "Robust wide-baseline stereo from maximally stable extremal regions," Image and vision computing 22.10 (2004): 761-767, which are incorporated herein by reference. However, other approaches are also contemplated herein.

For example, the feature detector 13 may be adapted for calculating, e.g. for each of the plurality of volumetric images, or each of a subset thereof, a blob detection spatial filter and/or applying a blob detection method, such as a Laplacian of Gaussian filter, a difference of Gaussians filter, a Harris filter, a Harris-Laplace filter, a Mongo-Ampére method, a Hessian-Laplace filter, an affine adapted differential blob detection filter, a watershed-based blob detection, a maximally stable extremal region (MSER) detection and/or a local SIFT- or SURF-like method.

For example, a Laplacian of Gaussian (LoG) may be calculated for each of the plurality of volumetric images, or each of a subset thereof, e.g. by applying:

$$\nabla^2 L = L_{xx} + L_{yy} + L_{zz},$$

where $L(x, y, z; \sigma) = g(x, y, z, \sigma) * f(x, y, z)$, where f indicates the volumetric image operated on, g indicates a Gaussian kernel function and * refers to the convolution operator.

The result may be normalized, e.g. by calculating a scale-normalized LoG, e.g. $\sigma^2 \nabla^2 L$, where $\sigma$ refers to a structure scale factor, to enable a scale-invariant analysis.

The features may be detected and identified by their locations $(\hat{x}, \hat{y}, \hat{z})$, e.g. their locations and structure scale factors $\sigma$, e.g. by $$(\hat{x}, \hat{y}, \hat{z}; \hat{\sigma}) = \mathrm{argminmax}_{x, y, z, \sigma} \sigma^2 \nabla^2 L$$

The device may also comprise a segmentation unit 15 for performing a segmentation of the structure corresponding to a detected feature in at least the image in which the feature was detected, e.g. a joint segmentation in a plurality of the plurality of images. For example, the segmentation may be performed in accordance with a segmentation approach known in the art. The segmentation may be specific to a region around the detected location. The segmentation may be limited to a region around the detected location that is, for example, determined by the detected scale.

Where reference is made to the subset of the plurality of volumetric images on which the feature detector 13 operates, this subset may particularly exclude the reference volumetric image referred to hereinbelow.

The device also comprises a marker generator 14 for generating a plurality of references indicating feature positions of a subset of the plurality of detected image features, in which said subset corresponds to the detected image features that are classified as difficult to discern on a reference volumetric image in the plurality of registered volumetric images based on a (e.g. numerical) classification and/or a (e.g. numerical) visibility criterium, the classification and/or criterium taking the noise model into account.

For example, the reference volumetric image may be representative of a conventional computed tomography image as obtained or derived from the spectral computed tomography acquisition sequence, for example a virtual non-contrast image. Likewise, the subset of the volumetric images referred to hereinabove may be the other spectral images.

Thus, in this step, the features, e.g. key points of potential interest, may be analyzed and alerts may be identified, e.g. situations in which a finding could not be seen or could barely be seen in the reference image, e.g. the conventional or virtual non contrast image, while it could be more easily seen in one of the remaining images, e.g. the spectral results.

The marker generator 14 may be adapted for determining the visibility criterium for each detected feature taking the identified location and the identified scale of each detected image feature into account.

The marker generator 14 may be adapted for performing the (e.g. numerical) classification by applying a machine learning approach as known in the art, for example, a deep learning approach, a random forest approach and/or a support vector machine approach, embodiments not being limited thereto. For example, a classifier or classification algorithm may be obtained by trained using a supervised learning technique, e.g. based on an an annotated cohort of cases.

The marker generator 14 may be adapted for estimating a contrast to noise ratio (CNR) for each image feature in at least the image i in which the feature was detected. For example, $$CNR_S = \frac{|C_A - C_B|}{n(\hat{x}, \hat{y}, \hat{z})},$$

may be calculated, in which | . . . | denotes the absolute value, $n(\hat{x}, \hat{y}, \hat{z})$ is the noise, e.g. obtained by the noise model, at the point $(\hat{x}, \hat{y}, \hat{z})$, e.g. corresponding to a detected feature, of an image i, $C_A$ is the median voxel value of a sphere around the point $(\hat{x}, \hat{y}, \hat{z})$ in the image i, and $C_B$ is the median voxel value of a spherical shell around the point $(\hat{x}, \hat{y}, \hat{z})$ in the image i, e.g. in which the radius of the sphere is equal to or smaller than the inner radius of the spherical shell. For example, the sphere may have a radius of $\hat{\sigma}\sqrt{3}$, and the spherical shell may have an inner radius of $\hat{\sigma}\sqrt{3}$ and an outer radius of $\sqrt{3}^3\sqrt{2}\hat{\sigma}$. Alternatively, instead of said sphere, a region determined by the segmentation unit may be used, and instead of the spherical shell, a region around the region determined by the segmentation unit may be used.

The marker generator 14 may be adapted for calculating the standard deviation $STD_s$ of the voxel values in a sphere around the point $(\hat{x}, \hat{y}, \hat{z})$ in the image i. For example, this sphere may have a radius that corresponds to the sphere used for calculating the CNR, e.g. $\hat{\sigma}\sqrt{3}$. Alternatively, instead of said sphere, a region determined by the segmentation unit may be used.

Furthermore, the marker generator 14 may be adapted for estimating in the reference image V the contrast to noise ratio of the feature. This CNR may be calculated for the reference image V in substantially the same manner as the CNR was calculated for that feature in the other image i. For example, $$CNR_C = \frac{|C_A - C_B|}{n(\hat{x}, \hat{y}, \hat{z})},$$

may be calculated, where | . . . | indicates an absolute value, $n(\hat{x}, \hat{y}, \hat{z})$ is the noise, e.g. obtained by the noise model, at the point $(\hat{x}, \hat{y}, \hat{z})$, e.g. corresponding to a detected feature, of the reference image V, $C_A$ is the median voxel value of a sphere around the point $(\hat{x}, \hat{y}, \hat{z})$ in the image V, and $C_B$ is the median voxel value of a spherical shell around the point $(\hat{x}, \hat{y}, \hat{z})$ in the image V, e.g. in which the radius of the sphere is equal to or smaller than the inner radius of the spherical shell. For example, the sphere may have a radius of $\hat{\sigma}\sqrt{3}$, and the spherical shell may have an inner radius of $\hat{\sigma}\sqrt{3}$ and an outer radius of $\sqrt{3^3}\sqrt{2}\hat{\sigma}$.

Alternatively, instead of said sphere, a region determined by the segmentation unit may be used, and instead of the spherical shell, a region around the region determined by the segmentation unit may be used.

le;.4qThe marker generator 14 may be adapted for calculating a normalized cross-correlation NCC between spheres around the point $(\hat{x}, \hat{y}, \hat{z})$ in respectively the reference image V and at least the image i in which the feature was detected. For example, these spheres may have a radius $\hat{\sigma}\alpha$, e.g. in which $\alpha$ is a controllable parameter, e.g. a configurable parameter. Alternatively, instead of said spheres, regions determined by the segmentation unit may be used.

The marker generator 14 may be adapted for calculating the mutual information MI between spheres around the point $(\hat{x}, \hat{y}, \hat{z})$ in respectively the reference image V and at least the image i in which the feature was detected. For example, these spheres may have a radius $\hat{\sigma}\beta$, e.g. in which $\beta$ is a controllable parameter, e.g. a configurable parameter. Alternatively, instead of said spheres, regions determined by the segmentation unit may be used.

The marker generator 14 may be adapted for determining a plurality of visibility criteria for each detected feature taking the identified location and the identified scale of each detected image feature into account.

The marker generator 14 may be adapted for classifying a detected feature as difficult to discern on the reference volumetric image if, for example a predetermined number, for example one, of the visibility criteria is met.

The plurality of visibility criteria may comprise:

$\hat{\sigma}\sqrt{3} \, CNR_c < t_1,$ $\hat{\sigma}\sqrt{3} \, CNR_s > t_2,$

-continued $\frac{CNR_s}{CNR_c} > t_3,$ $\hat{\sigma}\sqrt{3}\,(CNR_s - CNR_c) > t_4,$ $\hat{\sigma}\sqrt{3} \, CNR_c > t_5,$ $\frac{STD_s}{n(\hat{x}, \hat{y}, \hat{z})} < t_6,$ $V(\hat{x}, \hat{y}, \hat{z}) > t_7,$ $V(\hat{x}, \hat{y}, \hat{z}) < t_8,$ $NCC < t_9,$ , and/or $MI < t_{10},$ where $t_1$ to $t_{10}$ refer to predetermined or controllable, e.g. configurable, thresholds.

The marker generator may be adapted for excluding overlapping detected features that were classified as difficult to discern on the reference volumetric image, e.g. excluding all but one as representative of the detected region.

The marker generator may be adapted for excluding detected features based on a ratio of the CNR determined for the image i and the CNR determined for the reference image V, $\frac{CNR_s}{CNR_c},$ predetermined or configurable number k of the highest ranking CNR ratios may be reported.

Figure 3:
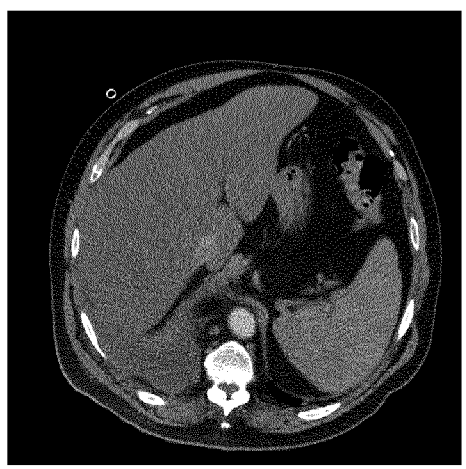
FIG. 3 shows a conventional CT image.
Figure 4:
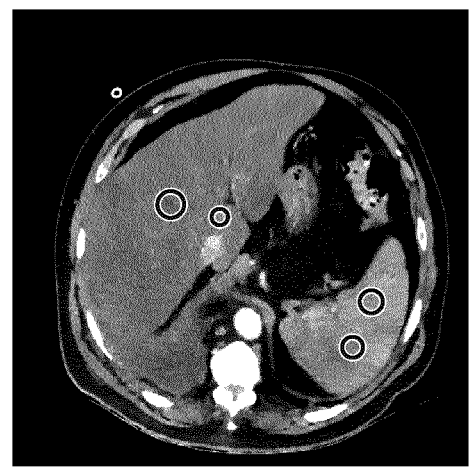
FIG. 4 shows a corresponding mono-energetic spectral image at 40 keV having a plurality of references indicated thereon in accordance with embodiments of the present invention.
Figure 5:
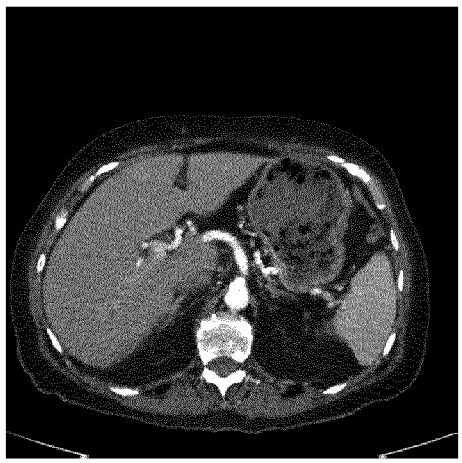
FIG. 5 shows a conventional CT image.
Figure 6:
FIG. 6 shows a corresponding mono-energetic spectral image at 40 keV having a plurality of references indicated thereon in accordance with embodiments of the present invention.
Figure 7:
FIG. 7 shows a conventional CT image.
Figure 8:
FIG. 8 shows a corresponding mono-energetic spectral image at 40 keV in accordance with embodiments of the present invention.

The device may comprise an output unit 16 for outputting, e.g. displaying, the reference image having locations of the plurality of references indicated thereon. Furthermore, optionally, the indications of the plurality of references on the reference image may also be indicative of the detected feature scale. Referring to FIGS. 3 and 4, respectively a conventional CT image, e.g. virtual non-contrast image, and a mono-energetic spectral image at 40 keV are shown, in which the circles on the latter indicate the plurality of references generated. For example, the centre of each circle may indicate the corresponding location and the radius of each circle may indicate the feature scale, e.g. may be proportional to the finding radius. FIGS. 5 and 6 show, likewise, another example, i.e. respectively a conventional CT image and a mono-energetic spectral image at 40 keV having the generated plurality of references marked thereon. In these examples, the conventional CT image is selected as the reference image, and features of interest are detected in the mono-energetic spectral image. It should be noted that, in embodiments in accordance with the present invention, the plurality of references may be indicated on the conventional CT image. However, for emphasis and ease of interpretation, the references are indicated on the mono-energetic spectral image in these examples. In another similar example, shown in FIG. 7 and FIG. 8, even though features could be found in the 40 keV mono-energetic spectral image shown in FIG. 8, no references were generated, e.g. the visibility of the features could be considered sufficient in the conventional CT image. This illustrates that, where a feature detection algorithm could, typically, generate false positives in a complex image, such as in the present example, advantageously, this does not need to imply that superfluous references for drawing the attention of a user are generated.

In a second aspect, embodiments of the present invention also relate to a computed tomography workstation comprising an image processing device in accordance with embodiments of the first aspect of the present invention. For example, the workstation may be adapted for visually presenting the references generated by the marker generator in a reading environment. For example, the references may be generated in real-time, e.g. while viewing the images on the workstation.

Embodiments of the present invention also relate to a computed tomography console comprising an image processing device in accordance with embodiments of the first aspect of the present invention. For example, the references may be generated as a preprocessing for later evaluation on a workstation. Furthermore, the console may be adapted for automatically generating the spectral results in which the references were detected.

In a third aspect, embodiments of the present invention also relate to a spectral computed tomography system comprising an image processing device in accordance with embodiments of the first aspect of the present invention. For example, embodiments of the present invention may relate to a spectral computed tomography system such as the imaging system 100 described hereinbelow in relation to FIG. 9.

Figure 9:
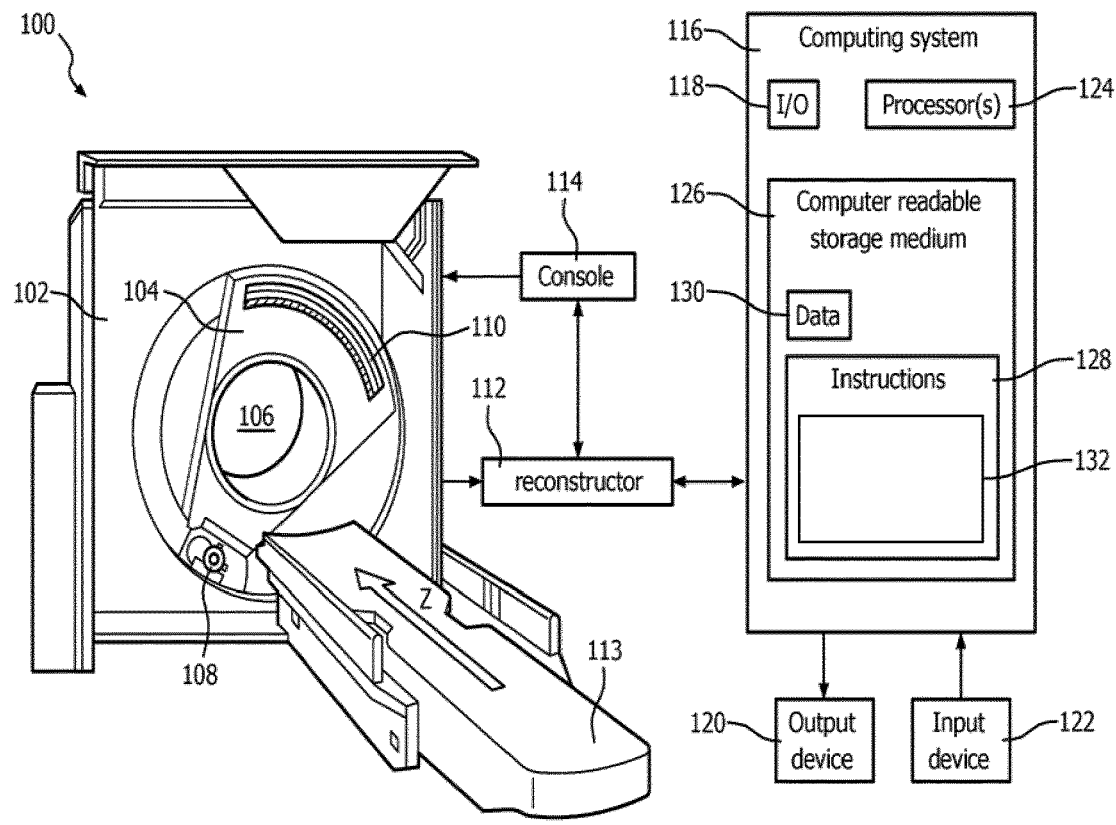
FIG. 9 shows a computed tomography system in accordance with embodiments of the present invention.

FIG. 9 illustrates an imaging system 100 comprising a spectral computed tomography (Spectral CT) scanner. The imaging system 100 may comprise a generally stationary gantry 102 and a rotating gantry 104. The rotating gantry 104 may be rotatably supported by the stationary gantry 102 and may rotate around an examination region 106 about a longitudinal axis Z.

A radiation source 108, such as an x-ray tube, may be rotatably supported by the rotating gantry 104, e.g. such as to rotate with this rotating gantry 104, and may be adapted for emitting poly-energetic radiation that traverses the examination region 106. The radiation source 108 may comprise, or consist of, a single broad spectrum x-ray tube. Alternatively, the radiation source may be adapted for controllably switching between at least two different photon emission spectra, e.g. switching between at least tow different peak emission voltages, such as 80 kVp, 140 kVp, etc., during scanning In another variation, the radiation source 108 may comprise two or more x-ray tubes configured to emit radiation with different mean spectrums. In another variation, the radiation source 108 may comprise a combination of the above.

A radiation sensitive detector array 110 may subtend an angular arc opposite the radiation source 108 across the examination region 106. The array 110 may include one or more rows of detectors arranged with respect to each other along the Z-axis direction. The array 110 may be adapted for detecting radiation traversing the examination region 106, and generating signals indicative thereof. The array 110 may comprise a dual-energy detector with at least two radiation sensitive detector elements having different x-ray energy sensitivities, e.g. at least two scintillators and at least two corresponding photosensors having corresponding optical sensitivities. The radiation sensitive detector array 110 may alternatively or additionally comprise a direct conversion detector, such as a CdTe, CdZnTe or other direct conversion detector known in the art.

The system may comprise a reconstructor 112 for reconstructing the signals output by the detector array 110. This may include decomposing the signal into various energy dependent components. The reconstructor 112 may be adapted for reconstructing the energy dependent components and generating one or more images corresponding to one or more different energies. The reconstructor 112 may also combine the energy dependent components to generate non-spectral image data.

The system may comprise a subject support 113, such as a couch, for supporting an object or subject in the examination region. The system may also comprise an operator console 114, e.g. a general purpose computer programmed for controlling or monitoring the system 100 and/or for providing a user interface for an operator. The console 114 may includes a human readable output device such as a monitor or display and an input device such as a keyboard and mouse. Software resident on the console 114 may allow the operator to interact with the scanner 100 via a graphical user interface (GUI) or otherwise. This interaction may include selecting a spectral imaging protocol or a non-spectral imaging protocol, initiating scanning, etc.

The imaging system 100 may be operably connected to a workstation, e.g. computing system 116, such as a computer, that may comprise an input/output (I/O) interface 118 for facilitating communication with the spectral CT scanner. The imaging system 100 may comprise the computing system 116 as a system-level integrated component, or the imaging system 100 may be adapted for communicating with a stand-alone computing system 116, e.g. to transmit image data to the computing system 116.

The computing system 116 may further comprise an output device 120. The output device or output devices may comprise, for example, a display monitor, a film printer, a paper printer and/or an audio output for audio feedback. The computing system may also comprise an input device 122 or input devices, such as a mouse, a keyboard, a touch interface and/or a voice recognition interface. The computing system 116 may also comprise at least one processor 124, such as a central processing unit (CPU), a microprocessor, a dedicated application-specific integrated circuit (ASIC) for processing and/or an appropriately configured programmable hardware processor such as a field-programmable gate array. The computing system may comprise a computer readable storage medium 126, e.g. a non-transitory memory such as a physical digital memory. The computer readable storage medium 126 may store computer readable instructions 128 and data 130. The at least one processor 124 may be adapted for executing the computer readable instructions 128. The at least one processor 126 may also execute computer readable instructions carried by a signal, carrier wave or other transitory medium. Alternatively or additionally, the at least one processor may be physically configured to embody the instructions 128, e.g. entirely or in part, without necessarily requiring memory storage of these instructions, e.g. by configuration of a field-programmable gate array or an ASIC specifically designed to carry out at least a part of the instructions.

The computing system may be programmed, e.g. in accordance with the computer readable instructions referred to hereinabove, to implement an image processing device 10 in accordance with embodiments of the first aspect of the present invention.

The instructions 128 may comprise an image processing algorithm 132 for performing a method in accordance with embodiments of a fourth aspect of the present invention.

In a further aspect, embodiments of the present invention also relate to a method for generating a plurality of references indicating image features that are classified as difficult to discern on a reference volumetric image. The method comprises receiving volumetric image data organized in voxels, in which the volumetric image data comprises a plurality of registered volumetric images of an imaged object. The method comprises generating a noise model indicative of a spatial distribution of noise in each of the plurality of registered volumetric images, and detecting a plurality of image features taking the volumetric image data into account. The method also comprises generating the plurality of references indicating feature positions of a subset of the plurality of detected image features, in which the subset corresponds to the detected image features that are classified as difficult to discern on a reference volumetric image in the plurality of registered volumetric images based on a (e.g. numerical) classification and/or a (e.g. numerical) visibility criterium. The classification and/or the visibility criterium takes the or each noise model into account.

Details of methods in accordance with embodiments of the present invention shall be clear in relation to the description provided hereinabove relating to embodiments of the first aspect of the present invention. Particularly, functions performed by the device in accordance with embodiments of the present invention shall be understood as constituting corresponding steps and/or features of a method in accordance with embodiments of the present invention.

Figure 10:
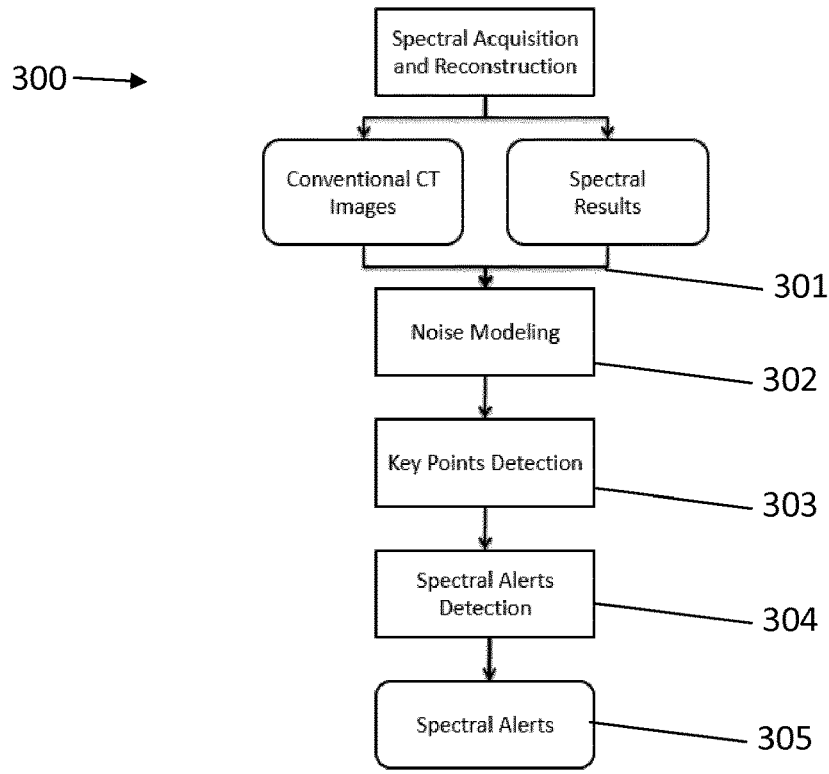
FIG. 10 shows an exemplary method in accordance with embodiments of the present invention.

FIG. 10 illustrates an exemplary method 300 in accordance with embodiments of the present invention.

The method 300 comprises receiving volumetric image data 301 organized in voxels, in which the volumetric image data comprises a plurality of registered volumetric images of an imaged object. For example, receiving the volumetric data 301 may comprise receiving a reference image, e.g. a conventional CT image, e.g. a virtual non-contrast image, and a plurality of spectral images, e.g. spectral results. This conventional CT image and these spectral images may be obtained by a spectral CT acquisition and reconstruction.

The method comprises generating 302 a noise model, e.g. a plurality of noise models, indicative of a spatial distribution of noise in each of the plurality of registered volumetric images.

The method comprises detecting 303 a plurality of image features, e.g. key points of interest, taking the volumetric image data into account.

The method also comprises generating 304 the plurality of references, e.g. spectral alerts, indicating feature positions of a subset of the plurality of detected image features, in which the subset corresponds to the detected image features that are classified as difficult to discern on a reference volumetric image in the plurality of registered volumetric images based on a (e.g. numerical) classification and/or a (e.g. numerical) visibility criterium. The classification and/or the visibility criterium takes the or each noise model into account.

The method may also comprise outputting 305 the references, e.g. spectral results. For example, this may comprise displaying the reference image annotated with the references. This may also comprise providing a user interface for enabling a user to select a reference, e.g. a spectral alert, and in response to such selection, displaying another image of the plurality of images, e.g. displaying the image in which the feature was detected.

In a further aspect, the present invention also relates to a computer readable storage medium encoded with one or more computer executable instructions, which, when executed by a processor of a computing system, causes the computing system to perform a method in accordance with embodiments of the present invention.

The invention claimed is:

1. An image processing device, comprising:
a data input for receiving volumetric image data organized in voxels, the volumetric image data comprising a plurality of registered volumetric images of an imaged object;
a noise modeler for generating a noise model indicative of a spatial distribution of noise in each of the plurality of registered volumetric images;
a feature detector for detecting a plurality of image features taking said volumetric image data into account; and
a marker generator for generating a plurality of references indicating feature positions of a subset of the plurality of detected image features, wherein said subset corresponds to the detected image features that are classified as difficult to discern on a reference volumetric image in the plurality of registered volumetric images based on a classification and/or a visibility criterium, wherein the classification and/or the visibility criterium takes the noise model into account.

2. The image processing device of claim 1, wherein the data input is configured to receive the volumetric image data in the form of the plurality of registered volumetric images obtained and/or derived from a single spectral computed tomography acquisition sequence.

3. The image processing device of claim 2, wherein the reference volumetric image is representative of a conventional computed tomography image as obtained by or derived from the spectral computed tomography acquisition sequence.

4. The image processing device of claim 1, wherein the feature detector is configured to identify a location and a scale of each detected image feature, and wherein the marker generator is configured to determine a plurality of visibility criteria for each detected feature taking the identified location and the identified scale of each detected image feature into account.

5. The image processing device of claim 4, wherein the marker generator is configured to classify a detected image feature as difficult to discern on the reference volumetric image if a predetermined number of the visibility criteria is met.

6. The image processing device of claim 1, wherein the marker generator is configured to estimate a contrast to noise ratio for each image feature in at least the image in which the image feature was detected and/or to estimate a contrast to noise ratio for each image feature in the reference image.

7. The image processing device of claim 1, wherein the marker generator is configured to, for each image feature, calculate a standard deviation of the voxel values in a region around the location of the image feature in the image in which the image feature was detected.

8. The image processing device of claim 1, wherein the marker generator is configured to, for each image feature, calculate a normalized cross-correlation and/or a mutual information between regions around the location of the image feature in respectively the reference image and at least the image in which the image feature was detected.

9. The image processing device of claim 1, comprising a segmentation unit for performing a segmentation of the structure corresponding to a detected feature in at least the image in which the feature was detected.

10. The image processing device of claim 1, wherein the feature detector is configured to calculate, for each of the plurality of volumetric images or each of a subset thereof, a scale-normalized Laplacian of Gaussian.

11. The image processing device of claim 1, wherein the noise modeler is configured to estimate the noise model using a Monte-Carlo estimation method, an analytical method, and/or a direct extraction technique.

12. A method for generating a plurality of references indicating image features that are classified as difficult to discern on a reference volumetric image, the method comprising:

receiving volumetric image data organized in voxels, the volumetric image data comprising a plurality of registered volumetric images of an imaged object;

generating a noise model indicative of a spatial distribution of noise in each of the plurality of registered volumetric images;

detecting a plurality of image features taking the volumetric image data into account; and generating the plurality of references indicating feature positions of a subset of the plurality of detected image features, wherein the subset corresponds to the detected image features that are classified as difficult to discern on a reference volumetric image in the plurality of registered volumetric images based on a numerical classification and/or a visibility criterium, wherein the classification and/or the visibility criterium takes the noise model into account.

13. A non-transitory computer readable storage medium encoded with one or more computer executable instructions, which, when executed by a processor of a computing system, causes the computing system to perform a method in accordance with claim claim 12.

* * * * *